(12) United States Patent
Martz

(10) Patent No.: US 10,166,337 B2
(45) Date of Patent: Jan. 1, 2019

(54) HAND-ACTUATED SYRINGE WITH VACUUM CHAMBER FOR AUTO REFILL

(71) Applicant: LIEBEL-FLARSHEIM COMPANY LLC, Cincinnati, OH (US)

(72) Inventor: Kevin R. Martz, St. Louis, MO (US)

(73) Assignee: LIEBEL-FLARSHEIM COMPANY LLC, Cincinnati, OH (US)

( * ) Notice: Subject to any disclaimer, the term of this patent is extended or adjusted under 35 U.S.C. 154(b) by 0 days.

(21) Appl. No.: 15/214,077

(22) Filed: Jul. 19, 2016

(65) Prior Publication Data

US 2017/0028133 A1 Feb. 2, 2017

Related U.S. Application Data

(63) Continuation of application No. 13/146,299, filed as application No. PCT/US2010/023125 on Feb. 4, 2010.

(Continued)

(51) Int. Cl.
| | |
|---|---|
| A61M 5/20 | (2006.01) |
| A61M 5/178 | (2006.01) |
| A61M 5/00 | (2006.01) |
| A61J 1/10 | (2006.01) |
| A61M 39/24 | (2006.01) |
| A61M 5/31 | (2006.01) |

(52) U.S. Cl.
CPC ............... A61M 5/204 (2013.01); A61J 1/10 (2013.01); A61M 5/007 (2013.01); A61M 5/1782 (2013.01); A61M 39/24 (2013.01); A61M 2005/3115 (2013.01)

(58) Field of Classification Search
CPC .... A61M 5/204; A61M 5/1782; A61M 5/007; A61M 2005/3115; A61M 39/24
See application file for complete search history.

(56) References Cited

U.S. PATENT DOCUMENTS

| | | | |
|---|---|---|---|
| 3,831,602 A | * 8/1974 | Broadwin | ......... A61M 5/31548 222/309 |
| 5,512,054 A | 4/1996 | Morningstar | |
| | (Continued) | | |

FOREIGN PATENT DOCUMENTS

| | | |
|---|---|---|
| DE | 19947185 | 4/2001 |
| EP | 1084724 | 3/2001 |
| | (Continued) | |

*Primary Examiner* — Jenna Zhang
(74) *Attorney, Agent, or Firm* — Marsh Fischmann & Breyfogle LLP

(57) ABSTRACT

A hand-activated syringe (14) is disclosed that uses a vacuum to retract a plunger (54) of the syringe (14) to draw fluid into a syringe body (18). A first seal (76) with the plunger (54) and a second seal (64) with the plunger (54) define a vacuum chamber (82). The spacing between the first seal (76) and the second seal (64) changes in response to the plunger (54) moving relative to the syringe body (18). Advancing the plunger (54) in a direction associated with a discharge stroke creates or increases a vacuum within the vacuum chamber (82) by increasing a spacing between the first seal (76) and the second seal (64). This vacuum thereafter may be used to retract the plunger (54) by decreasing a spacing between the first seal (76) and the second seal (64), and to thereby draw fluid into the syringe (14) from a fluid source (86).

23 Claims, 4 Drawing Sheets

Related U.S. Application Data

(60) Provisional application No. 61/149,718, filed on Feb. 4, 2009.

(56) References Cited

U.S. PATENT DOCUMENTS

| | | | | |
|---|---|---|---|---|
| 5,807,340 | A | * | 9/1998 | Pokras ................ A61M 5/204 604/183 |
| 6,719,728 | B2 | * | 4/2004 | Mason ............... A61M 5/1424 604/131 |
| 6,989,000 | B2 | | 1/2006 | Schreijag et al. |
| 7,278,985 | B2 | * | 10/2007 | Ågerup ............ A61M 5/14216 604/181 |
| 2006/0253074 | A1 | | 11/2006 | Thayer |
| 2007/0179452 | A1 | * | 8/2007 | Kosinski ........... A61M 5/31511 604/218 |
| 2007/0250003 | A1 | | 10/2007 | Bare et al. |
| 2008/0264261 | A1 | * | 10/2008 | Kavazov .............. A61J 1/2096 96/193 |
| 2011/0224610 | A1 | * | 9/2011 | Lum ..................... A61M 5/38 604/125 |
| 2011/0224612 | A1 | * | 9/2011 | Lum ................. A61M 5/31511 604/125 |
| 2011/0224642 | A1 | * | 9/2011 | Fojtik ................. A61M 5/204 604/500 |

FOREIGN PATENT DOCUMENTS

| | | | | |
|---|---|---|---|---|
| EP | 1084724 | A1 | * 3/2001 | ......... A61B 10/0045 |
| JP | 07-227425 | | 8/1995 | |
| JP | 2003-199826 | | 7/2003 | |
| WO | 2004039441 | | 5/2004 | |
| WO | 2004110530 | | 12/2004 | |

* cited by examiner

HAND-ACTUATED SYRINGE WITH VACUUM CHAMBER FOR AUTO REFILL

RELATED APPLICATIONS

This application is a continuation of U.S. patent application Ser. No. 13/146,299, filed on Jul. 26, 2011, which is a U.S. National Stage of PCT/US2010/023125, filed on Feb. 4, 2010, which claims priority to U.S. Provisional Patent Application No. 61/149,718, filed on Feb. 4, 2009 and entitled "HAND-ACTUATED SYRINGE WITH VACUUM CHAMBER FOR AUTO REFILL." Priority is claimed to each patent application set forth in this Cross-Reference to Related Applications section.

FIELD OF THE INVENTION

The present invention generally relates to filling hand-actuated syringes.

BACKGROUND

Hand-held, hand-powered (e.g., hand-actuated) syringes may be used for cardiac catheter lab procedures and special angiographic procedures. For instance, the syringe may need to be filled with medical fluid (e.g., contrast media for use in medical imaging) one or more times for a given procedure. In this regard, a first syringe is typically interconnected with a bottle by using a combination of a syringe needle and a piercable membrane/diaphragm of the bottle, or by using a combination of a syringe luer fitting and a vented spike associated with the bottle. Once interconnected with the bottle, a user or clinician (typically a nurse) manually retracts the syringe plunger to draw medical fluid from within the bottle into the syringe. Upon being filled to a desired level, the syringe is disconnected from the bottle. A user (typically a physician) then injects the medical fluid from within the syringe into the patient (e.g., typically through a catheter already positioned in the patient's vasculature).

Quite often, more medical fluid than is initially filled into the syringe is desired to complete the medical procedure (e.g., angiographic imaging). As such, another syringe is filled in the manner described above, or the same syringe is refilled in a similar fashion to that described above. In either case, it could be said that one or both time and materials (e.g., multiple syringes) are wasted.

SUMMARY

As used herein, the phrase "fluidly isolated" or the like describes a relationship between components where fluid is, at least temporarily, not able to flow between the components. For example, where two components are fluidly isolated from each other, fluid at that time is unable to flow from one component to the other component. Such an inability to flow may be due to one or more valves being positioned to prevent such flow between the two components.

As used herein, the phrases "fluidly interconnected, "in fluid communication with," "fluidly communicates with," or the like each describes a relationship between components where fluid is able to flow between the components in at least one circumstance. For example, "an injection device fluidly interconnected to a patient" describes a configuration where fluid is able to flow from the injection device, through any intermediate components (e.g., tubing, connectors), and to the patient (e.g., into the vasculature of the patient).

A first aspect of the present invention is embodied by a syringe that includes a syringe body having a discharge port defined therein. In addition, the syringe includes a plunger that is movable relative to the syringe body and that includes a plunger head. The plunger head is disposed within the syringe body and is movable relative to the syringe body. There is a first seal with the plunger, where the plunger moves relative to this first seal.

A number of feature refinements and additional features are applicable to the first aspect of the present invention. These feature refinements and additional features may be used individually or in any combination. As such, each of the following features that will be discussed may be, but are not required to be, used with any other feature or combination of features of the first aspect. The following discussion is applicable to the first aspect, up to the start of the discussion of a second aspect of the present invention.

The term "seal" is being used herein to define a region that prevents fluid from passing by the location of the seal. Unless otherwise specified, a seal may be defined in any appropriate manner. A seal may be defined by an interface between two or more components. In the case of the first aspect, there is a first seal with the plunger. As such, the first seal prevents fluid from passing by the plunger at the location of the first seal.

The location of the first seal is subject to a number of characterizations. The plunger head may move away from the first seal and toward the discharge port during a fluid discharge stroke—a movement of the plunger relative to the syringe body for purposes of discharging fluid from the syringe. The plunger head may be characterized as being between the discharge port and the first seal when the plunger is in its fully retracted position (e.g., where the fully retracted position may be associated with a maximum amount of fluid being within the syringe for use in a subsequent fluid discharge operation).

The syringe may include a discharge chamber that is defined by a portion of an interior of the syringe body, along with the plunger head. A fluid to be discharged from the syringe may be contained within this discharge chamber. In one embodiment, it may be said that the discharge chamber is disposed on one side of the plunger head, while the first seal is disposed on an opposite side of the plunger head. This first seal may at least assist in defining a vacuum chamber, where this vacuum chamber and discharge chamber are thereby disposed on opposite sides of the plunger head within the syringe body. The phrase "vacuum chamber" means a chamber that is at a pressure that is less than the ambient pressure to which the syringe is exposed. The term "vacuum" encompasses any pressure that is less than ambient pressure. A vacuum pressure may also be referred to as negative pressure. A vacuum force may be a force that is exerted on an object by a negative pressure.

A vacuum chamber may be provided within the interior of the syringe body, and may include first and second closed or sealed ends. The first closed end of the above-noted vacuum chamber may be defined at least in part by the first seal. The first seal may be realized in any appropriate manner. For instance, one or more sealing members (e.g., O-rings) may be mounted to the syringe body so as to remain in a fixed position relative to the syringe body, and may engage the plunger (e.g., a plunger push rod that extends from the plunger head and beyond the syringe body). That is, the interface between a stationary O-ring and a movable plunger may define the first seal.

The second closed end of the vacuum chamber may be defined at least in part by the plunger head. Generally, there may be a second seal with the plunger, where this second seal moves along with the plunger (e.g., the second seal may be characterized as being maintained in a fixed position relative to the plunger, or stated another way this second seal may be characterized as staying in the same location with respect to the plunger head as the plunger head moves within and relative to the syringe body). The second seal may be realized in any appropriate manner. One or more sealing members (e.g., O-rings) may be mounted on the plunger (e.g., on the plunger head) and may engage an interior surface of the syringe body to define the second seal. In this case, the interface between such an O-ring(s) and the interior of the syringe body would define the second seal. Another option for defining the second seal is the interface between the plunger head itself and an interior of the syringe body. In each of these two instances, the location of the second seal will move along with the plunger.

Based upon the foregoing, at least one seal for the noted vacuum chamber may move relative to the syringe body (e.g., the above-noted second seal), while at least one seal for the vacuum chamber may be maintained in a fixed position relative to the syringe body (e.g., the above-noted first seal). Another characterization is that the spacing between the first and second seals (and thereby the size of the vacuum chamber) may change by a movement of the plunger relative to the syringe body.

A second aspect of the present invention is embodied by a syringe that includes a syringe body having a discharge port defined therein. This syringe also includes a plunger that is movable relative to the syringe body and that includes a plunger head. The plunger head is disposed within the syringe body and is movable relative to the syringe body. A discharge chamber of the syringe body is located on one side of the plunger head and is in fluid communication with the discharge port for the syringe body. Further, a vacuum chamber of the syringe body is located within the syringe body on another side of the plunger head and is fluidly isolated from the discharge chamber.

A number of feature refinements and additional features are applicable to the second aspect of the present invention. These feature refinements and additional features may be used individually or in any combination. As such, each of the following features that will be discussed may be, but are not required to be, used with any other feature or combination of features of the second aspect. The following discussion is applicable to the second aspect, up to the start of the discussion of a third aspect of the present invention.

Moving the plunger relative to the syringe body in a direction associated with a fluid discharge stroke for the syringe may decrease the volume of the discharge chamber, may increase the volume of the vacuum chamber, or both. There may be a first seal with the plunger (e.g., a plunger push rod), where the plunger may move relative to this first seal. There may be a second seal with the plunger (e.g., a plunger head), where this second seal may move along with the plunger. These first and second seals may each define a boundary for the vacuum chamber, and may be in accordance with the first and second seals discussed above in relation to the first aspect. Each of the various features discussed above in relation to the first aspect may be used by this second aspect, individually or in any combination.

A number of feature refinements and additional features are separately applicable to each of the first and second aspects of the present invention. These feature refinements and additional features may be used individually or in any combination. As such, each of the following features that will be discussed may be, but are not required to be, used with any other feature or combination of features of each of the first and second aspects. The following discussion is separately applicable to each of the first and second aspects, up to the start of the discussion of a third aspect of the present invention.

The syringe may be a hand-held, hand-powered or hand-activated syringe of any appropriate type. For instance, the syringe may include a plunger push rod that extends from the plunger head and beyond an end of the syringe body (e.g., opposite of the discharge port) such that it may be engaged by a user's thumb. An end of the plunger push rod that extends beyond the syringe body may include an appropriate actuation surface for engagement by an operator (e.g., thumb-actuated). The syringe may also be in the form of what is commonly known as a "control syringe"—a configuration where at least one loop extends from the barrel of the syringe for receiving a user's finger(s), and where a loop extends from an end of the plunger for receiving a user's thumb. Yet another option for the syringe is to have a pair of levers that are movably interconnected (e.g., by a pivot pin), where one lever is also movably interconnected with the syringe body (e.g., by a pivot pin), and where the other lever is movably interconnected with the plunger (e.g., by a pivot pin) such that that a single hand of a user may engage and manipulate the levers to change the position of the plunger relative to the syringe body. In any case, user-applied forces may be used to advance the plunger for a fluid discharge stroke in the case of each of the first and second aspects.

The syringe may include a first check valve to control flow out of the syringe body. In one embodiment, this first check valve is located within a discharge nozzle of the syringe. Other locations may be appropriate. The syringe body may include a fill port, and the syringe may further include a second check valve for this fill port (e.g., to control flow into the syringe body through the fill port). As such, a valve may fluidly isolate the syringe from a fluid source during a fluid discharge from the syringe (e.g., the second check valve), a valve may fluidly isolate a patient (interconnected with the discharge port of the syringe) from a fluid source during a syringe loading or refilling operation (e.g., the first check valve), or both.

Vacuum forces may provide the sole force for retracting the syringe plunger to load fluid into the syringe. However, one or more other forces may be used to facilitate retraction of the syringe plunger. For instance, one or more biasing members may be used to bias the plunger to/toward a fully retracted position. Any appropriate biasing member may be utilized, for instance, a spring. In this regard, one end of a biasing spring may be fixed to the plunger in an appropriate manner, while an opposite end of the spring may be fixed to the syringe body in an appropriate manner. Each biasing member may be fluidly isolated from fluid to be discharged from the syringe.

The syringe may be used for any appropriate application, for instance to inject fluid into a patient (e.g., via tubing mounted to a discharge nozzle of the syringe, and/or by a catheter or other access device inserted into the vasculature of the patient). A fluid delivery system of the invention may utilize a fluid source and any syringe described herein. The fluid source of such a fluid delivery system may be fluidly interconnected with a fill port of the syringe, and a check valve (e.g., the second check valve mentioned above) may be used to control the flow into the syringe from the fluid source. In one embodiment, a pressure head of the fluid source may be used to supplement or augment the vacuum force to retract the plunger for purposes of loading fluid into the syringe. In one embodiment, the fluid source is pressurized (e.g., by a pressurizing source), and this pressure may be used to supplement or augment the vacuum force to retract the plunger for purposes of loading fluid into the syringe. Any one or more of the supplemental forces described herein may be used with the vacuum force to retract the plunger for purposes of loading fluid into the syringe, including in any appropriate combination.

A third aspect of the present invention is embodied by a method for loading fluid into a syringe. In this method, a vacuum is created within a body of the syringe, and a plunger of the syringe is moved relative to the syringe body in a first direction using this vacuum. A medical fluid (e.g., contrast media for use in a medical imaging procedure) is drawn into the syringe body due to this movement of the syringe plunger in the first direction.

A number of feature refinements and additional features are applicable to the third aspect of the present invention. These feature refinements and additional features may be used individually or in any combination. As such, each of the following features that will be discussed may be, but are not required to be, used with any other feature or combination of features of the third aspect. The remainder of this discussion is applicable to at least this third aspect. Initially, the syringe in accordance with each of the first and second aspects may be used in this third aspect.

The vacuum may be created by moving the plunger relative to the syringe body in a second direction. The syringe plunger may be moved in one direction (e.g., a second direction) to create the vacuum, and the syringe plunger may be moved in an opposite direction (e.g., the noted first direction) by the vacuum force to draw fluid into the syringe body. The noted first and second directions may be opposite of each other. The vacuum may be created by advancing the plunger without any medical fluid having been previously loaded into the syringe body (e.g., an empty configuration for the syringe). For instance, it may be such that only air or another gas is being discharged from the syringe by movement of the plunger that generates a vacuum (e.g., a movement in the noted second direction). However, the vacuum may be created while advancing the plunger relative to the syringe body to discharge medical fluid from the syringe. In one embodiment, the medical fluid that is discharged from the syringe by an advancement of the plunger (and which generates the vacuum) is of the same type as a medical fluid that is loaded into the syringe by a vacuum-assisted movement of the syringe plunger.

The entire force that retracts the plunger to load fluid into the syringe may be provided by a vacuum. Other forces may be used in combination with this vacuum to retract the syringe plunger. For instance, a movement of the plunger that creates the vacuum may also increase a spring force that acts on the syringe plunger, and that assists in retracting the plunger to draw fluid into the syringe. More generally, a biasing force may be exerted on the plunger and which biases the same toward/to its fully retracted position. The magnitude of this biasing force may increase as the plunger moves in a direction that also increases the absolute value of the force created by the vacuum. A pressure head may be used to retract the syringe plunger. Pressurizing a fluid source may also be used to retract the syringe plunger. Any one or more of these supplemental forces may be used with a vacuum to retract the plunger, individually or in any combination.

A first check valve may be opened when advancing the plunger relative to the syringe body in a direction that creates a vacuum (e.g., a check valve that controls a flow out of the syringe), a second check valve may be closed when advancing the plunger relative to the syringe body in a direction that creates a vacuum (e.g., a check valve that controls a flow from a fluid source into the syringe), or both. A first check valve may be closed when moving the plunger relative to the syringe body in a direction that draws fluid into the syringe body (e.g., a check valve that controls a flow out of the syringe), a second check valve may be opened when moving the plunger relative to the syringe body in a direction that draws fluid into the syringe body (e.g., a check valve that controls a flow from a fluid source into the syringe), or both.

A number of feature refinements and additional features are separately applicable to each of above-noted first, second, and third aspects of the present invention. These feature refinements and additional features may be used individually or in any combination in relation to each of the above-noted first, second, and third aspects of the present invention. Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a power injector includes "a syringe" alone does not mean that the power injector includes only a single syringe). Moreover, any failure to use phrases such as at least one also does not limit the corresponding feature to the singular (e.g., indicating that a power injector includes "a syringe" alone does not mean that the power injector includes only a single syringe). Finally, use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical).

DETAILED DESCRIPTION

Figure 1:
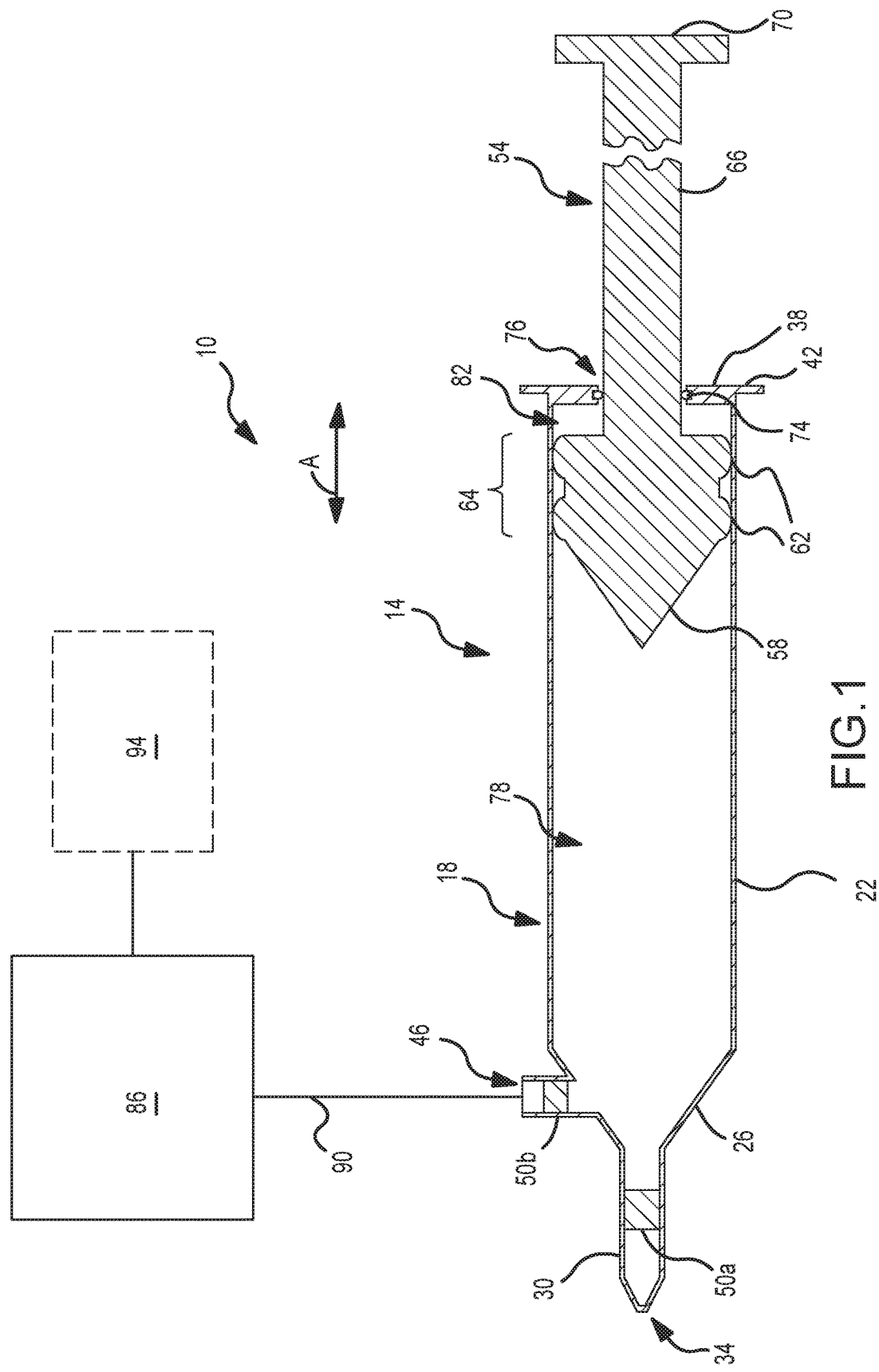
FIG. 1 is a schematic of one embodiment of a fluid delivery system having a vacuum-assisted refill syringe.

One embodiment of a fluid delivery system is illustrated in FIG. 1 and is identified by reference numeral 10. The fluid delivery system 10 includes a syringe 14 and a fluid source 86. Generally, the fluid delivery system 10 is configured to automatically refill the syringe 14 with fluid from the fluid source 86. The term "refill" encompasses providing any appropriate volume to the syringe 14, and specifically does not require that the entire fluid-containing volume of the syringe 14 be occupied by fluid from the fluid source 86 as a result of a refilling operation.

The syringe 14 includes a syringe body 18 and a plunger or push rod assembly 54 that extends within and that is movable relative to the syringe body 18. The syringe body 18 may be of any appropriate size, shape, configuration, and/or type. The syringe body 18 may be formed from any appropriate material or combination of materials. In one embodiment, the syringe body 18 is an integrally-formed structure (e.g., of one-piece construction; such that there are no joints of any kind between adjacent portions/sections of the syringe body 18). However, the syringe body 18 could be defined by two or more separately fabricated structures that are appropriately joined together.

The syringe body 18 includes a flange 42, a barrel 22 (e.g., cylindrical), a transition section 26 (e.g., in the form of a truncated cone; frustumly-shaped), and a discharge nozzle 30. The discharge nozzle 30 includes a discharge port 34. Fluid may be discharged from the syringe 14 through this discharge port 34. A check valve 50a may be disposed within the discharge nozzle 30, or more generally between the discharge port 34 and the push rod assembly 54. Preferably, all flow out of the syringe 14 is directed through the check valve 50a.

The syringe body 18 may also include a fill or refill port 46. A discharge from the fluid source 86 may be directed into the syringe 14 through this fill port 46. The fill port 46 may be disposed at any appropriate location relative to the syringe body 18. In the illustrated embodiment, the fill port 46 is disposed on the transition section 26 of the syringe body 18. Generally, it may be desirable for the fill port 46 to be located at or near the end of the discharge stroke of the push rod assembly 54. In any case, a check valve 50b may be disposed within the fill port 46, or more generally between the fluid source 86 and the interior of the syringe barrel 22. Preferably, all flow into the syringe 14 (from the fluid source 86) is directed through the check valve 50b.

The push rod assembly 54 extends within the syringe body 18, and furthermore is movable relative to the syringe body 18. The push rod assembly 54 includes a plunger head 58 and a plunger push rod 66 that extends from the plunger head 58. One or more annular sealing members 62 may be formed on a perimeter of the plunger head 58 and may engage an interior surface of the syringe body 18. Each such sealing member 62 may be of any appropriate size, shape, configuration, and/or type. Each sealing member 62 may be integrally-formed with the push rod assembly 54 as shown, although one or more sealing members could be separately formed and mounted on the plunger head 58 (e.g., an O-ring). Any sealing member that was separately mounted to the plunger head 58 would then become part of the plunger head 58.

Generally, the interface between the perimeter of the plunger head 58 and the interior of the syringe body 18 defines a second seal 64. Any appropriate shape for the perimeter of the plunger head 58 may be utilized to define the second seal 64 (e.g., different shapes of sealing members 62 may be appropriate; a cylindrical surface defining the perimeter of the plunger head 58 could be pressed against the interior of the syringe body 18 to define the second seal 64). In any case, fluid should be prevented from flowing past the second seal 64.

Since the plunger head 58 moves relative to the syringe body 18, so too does the second seal 64 and as indicated by the double-headed arrow A in FIG. 1. That is, the second seal 64 may be characterized as moving along with the push rod assembly 54 during use of the syringe 14. The second seal 64 may be characterized as being maintained in a fixed position relative to the push rod assembly 54. The second seal 64 may be characterized as staying in the same location with respect to the plunger head 58 as the plunger head 58 moves within and relative to the syringe body 18.

The plunger push rod 66 extends beyond a first end 38 of the syringe body 18 (where the first end 38 is opposite of the discharge port 34 in the illustrated embodiment). An actuation surface 70 is provided on an exposed end of the plunger push rod 66. A user may position a digit (e.g., a thumb) on this actuation surface 70 to advance the push rod assembly 54 toward the discharge nozzle 30 to discharge fluid from the syringe 14. Therefore, the syringe 14 may be characterized as being hand-actuated or hand-powered.

One or more sealing members 74 may be fixed relative to the syringe body 18 (e.g., mounted to the syringe body 18), and may engage the push rod assembly 54 to define a first seal 76. The push rod assembly 54 moves relative to this first seal 76—the first seal 76 may stay in the same location as the push rod assembly 54 is moved. In the illustrated embodiment, the sealing member 74 is at least generally disposed at the first end 38 of the syringe body 18, and engages the plunger push rod 66. Each such sealing member 74 may be of any appropriate size, shape, configuration, and/or type (e.g., an O-ring).

The plunger head 58 may be characterized as separating the interior of the syringe body 18 into a fluid or discharge chamber 78 and a vacuum chamber 82. The discharge chamber 78 may be characterized as being disposed on one side of the plunger head 58, while the vacuum chamber 82 may be characterized as being disposed on the opposite side of the plunger head 58. Generally, the discharge chamber 78 is disposed on the side of the plunger head 58 that fluidly communicates with the discharge port 34, while the vacuum chamber 82 is disposed on the opposite side of the plunger head 58 (e.g., on the "back" side of the plunger head 58). Therefore, the vacuum chamber 82 extends between the second seal 64 (e.g., defined by the engagement of the movable plunger head 58 with the interior of the syringe body 18) and the first seal 76 (e.g., defined by the engagement of the sealing member 74 with the push rod assembly 54, specifically the plunger push rod 66 in the illustrated embodiment).

The spacing between the first seal 76 and the second seal 64 changes in response to movement of the push rod assembly 54 relative to the syringe body 18. When the push rod assembly 54 is moved toward the discharge port 34 (in the direction associated with a fluid discharge stroke), the spacing between the first seal 76 and the second seal 64 increases (e.g., by a movement of the second seal 64 relative to the stationary first seal 76). This reduces the size of the discharge chamber 78 (e.g., to provide a fluid discharge from the syringe 14) and increases the size of the vacuum chamber 82. When the push rod assembly 54 is moved away from the discharge port 34 (in the direction associated with a fluid-loading operation), the spacing between the first seal 76 and the second seal 64 decreases (e.g., by a movement of the second seal 64 relative to the stationary first seal 76). This increases the size of the discharge chamber 78 (e.g., to accommodate the loading of fluid therein) and decreases the size of the vacuum chamber 82.

The fluid source 86 is fluidly interconnected with the syringe 14 by a fill or refill line 90 that extends to the refill port 46 of the syringe 14. Any appropriate fluid may be utilized by the fluid source 86 (e.g., contrast media; a flushing agent such as saline or any other biocompatible media). The fill line 90 may be in the form of a conduit of any appropriate type (e.g., medical tubing).

Figure 2A:
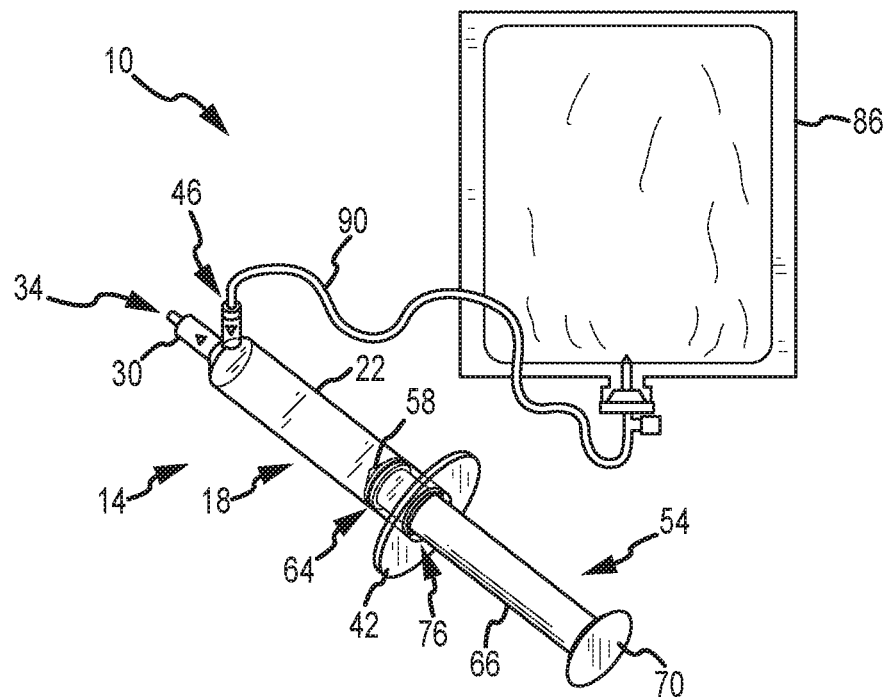
FIGS. 2A-C present a refill sequence for the vacuum-assisted refill syringe used by the fluid delivery system of FIG. 1.
Figure 2B:
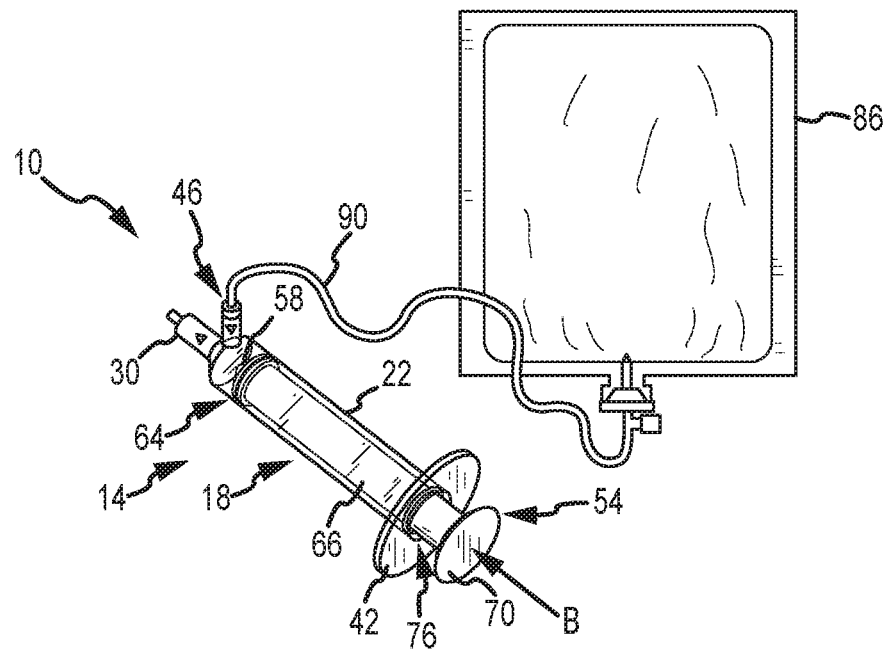
Figure 2C:
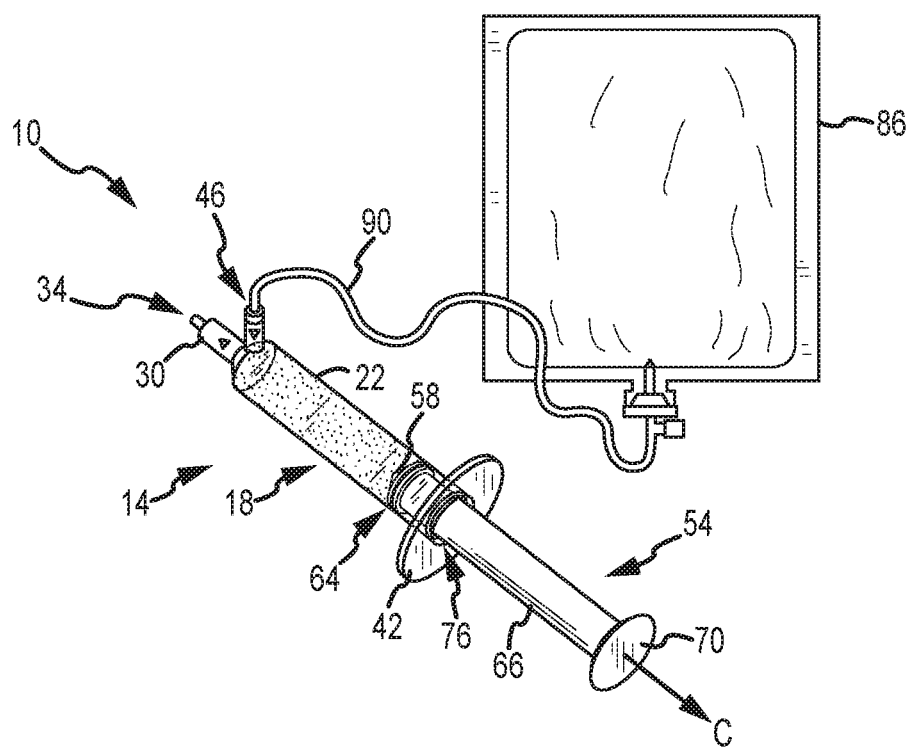

The vacuum chamber 82 may provide the sole or primary force that moves the push rod assembly 54 in a manner that fills or refills the syringe 14 with fluid from the fluid source 86. FIGS. 2A-C present one embodiment of a refill sequence that uses a vacuum force to retract the syringe push rod assembly 54. The push rod assembly 54 is in its fully retracted position in FIG. 2A. A user may engage the actuation surface 70 of the push rod assembly 54, and push the push rod assembly 54 in the direction of the discharge port 34 and as shown in FIG. 2B (e.g., a movement in the direction of the arrow B). This increases the size of the vacuum chamber 82 and simultaneously reduces the size of the discharge chamber 78 (e.g., by increasing the spacing between the first seal 76 and the second seal 64, where the first seal 76 remains stationary relative to the push rod assembly 54 and where the second seal 64 moves along with the push rod assembly 54). The check valve 50b should preclude any fluid from being discharged into the fluid source 86 at this time. Moreover, this motion of the push rod assembly 54 should cause the check valve 50a to open such that fluid is discharged from the syringe 14 (a certain differential pressure may be required to open the check valve 50a). In FIGS. 2A and 2B, this fluid may be in the form of air, such that a patient should not be fluidly interconnected with the syringe 14 at this time. In any case, the noted motion should also progressively reduce the pressure within the vacuum chamber 82 (e.g., the pressure within the vacuum chamber 82 should become "more negative" as the push rod assembly 54 is advanced on a fluid discharge stroke), or stated another way the absolute value of the negative pressure within the vacuum chamber 82 should increase by a movement of the push rod assembly 54 toward the discharge port 34.

When the push rod assembly 54 has reached the end of a desired fluid discharge stroke and the user releases the push rod assembly 54, the "suction forces" within the vacuum chamber 82 should move the push rod assembly 54 toward (e.g., back to) its fully retracted position (e.g., in the direction of the arrow C in FIG. 2C). That is, the negative pressure within the vacuum chamber 82 should retract the push rod assembly 54. Retraction of the push rod assembly 54 decreases the size of the vacuum chamber 82 and simultaneously increases the size of the discharge chamber 78 (e.g., by decreasing the spacing between the first seal 76 and the second seal 64, where the first seal 76 remains stationary relative to the push rod assembly 54 and where the second seal 64 moves along with the push rod assembly 54). The retraction of the push rod assembly 54 should open the check valve 54b to draw fluid from the fluid source 86 into the syringe 14 via the fill port 46 and as shown in FIG. 2C. It should be appreciated that this retraction of the push rod assembly 54 may be initiated from various different positions within the syringe barrel 22 (e.g., the plunger head 58 need not be at or near the transition section 26 when the user releases the push rod assembly 54, such that it is thereafter retracted via the negative pressure in the vacuum chamber 82).

With fluid having been loaded in the syringe 14 in the above-noted manner (e.g., FIG. 2C), a patient may be fluidly interconnected with the syringe 14 in any appropriate manner (e.g., via medial tubing mounted on the discharge nozzle 30 of the syringe 14, along with a catheter or any other vasculature access device that is directed into the vasculature of the patient). Moreover, a user may again engage the actuation surface 70 of the push rod assembly 54, and push the push rod assembly 54 in the direction of the discharge port 34 (e.g., in the direction of arrow B in FIG. 2B). This again progressively increases the size of the vacuum chamber 82 and progressively reduces the pressure within the vacuum chamber 82. This also progressively reduces the size of the discharge chamber 78 such that fluid is discharged out of the syringe 14 through the discharge port 34 in the above-noted manner. When the desired amount of fluid has been discharged from the syringe 14, the user may release the push rod assembly 54, and the "suction forces" within the vacuum chamber 82 should again move the push rod assembly 54 toward (e.g., back to) its fully retracted position (e.g., in the direction of arrow C in FIG. 2C). That is, the negative pressure within the vacuum chamber 82 should again retract the push rod assembly 54, where this retraction should open the check valve 54b to draw fluid from the fluid source 86 into the syringe 14 via the fill port 46. This fill/discharge cycle may be repeated any number of times.

The syringe 14 could be configured such that the push rod assembly 54 is initially disposed in an extended position within the syringe body 18 (e.g., at its minimum spacing with the discharge port 34), and then retained or locked in this position in any appropriate manner. That is, there would be a vacuum or a negative pressure within the vacuum chamber 82 at this time. A user could release the push rod assembly 54 to allow fluid to be initially loaded into the syringe 14 from the fluid source 86 in the above-noted manner, namely where the "suction force" within the vacuum chamber 82 would retract the push rod assembly 54 (e.g., to the fully retracted position shown FIG. 2C). Thereafter, any number of discharge/fill cycles could be repeated in accordance with the foregoing.

Figure 3:
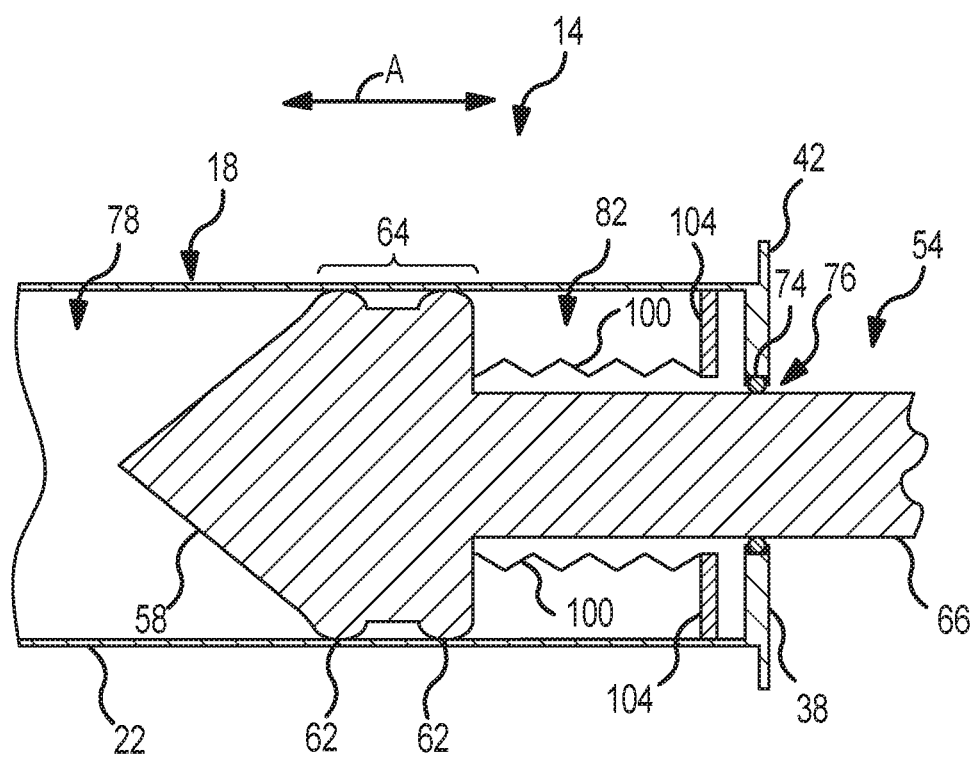
FIG. 3 illustrates the vacuum-assisted refill syringe used by the fluid delivery system of FIG. 1, with an optional supplemental return spring.

One or more forces could be utilized to supplement the vacuum force for retracting the syringe push rod assembly 54, to in turn load fluid into the syringe 14 from the fluid source 86 in the above-noted manner. For instance, the pressure head within the fluid source 86 may contribute to retracting the push rod assembly 54 to load fluid into the syringe 14 from the fluid source 86. The pressure source 86 could also be pressurized, for instance by a pressurizing source 94 that is fluidly interconnected with the fluid source 86. Another option is illustrated in FIG. 3, where one or more biasing members (e.g., a spring) are used to bias the push rod assembly 54 toward/to its fully retracted position. Generally, one end of the biasing member 100 may be fixed relative to the push rod assembly 54 (e.g., its plunger head 58), while another end of the biasing member 100 may be fixed relative to the syringe body 18 (e.g., by a spring anchor 104). In this case, advancing the push rod assembly 54 on a discharge stroke increases the magnitude of the spring force in the biasing member 100 (or stated another way, increases the magnitude of the biasing force). Once the push rod assembly 54 is released, this spring or biasing force, along with the suction force that has developed within the vacuum chamber 82, retracts the push rod assembly 54 to draw fluid into the syringe body 18 from the fluid source 86.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A method for operating a fluid delivery system that is separate from but connectable to a patient, said fluid delivery system comprising a syringe and a separate fluid source, said syringe comprising a syringe body, a plunger comprising a plunger head disposed within said syringe body, a vacuum chamber within said syringe body, a discharge chamber within said syringe body, a fill port to said discharge chamber, and a discharge port from said discharge chamber, wherein said plunger head is disposed between and separates said discharge chamber from said vacuum chamber such that said discharge chamber and said vacuum chamber are disposed on opposite sides of said plunger head within said syringe body, and wherein said plunger head fluidly isolates said vacuum chamber from said discharge chamber, said method comprising:

executing a first moving step comprising moving said plunger and said plunger head relative to said syringe body and in a discharge direction to discharge a gaseous fluid from said discharge chamber, while said discharge port is disconnected from said patient, and by said plunger head interfacing with said gaseous fluid within said discharge chamber;

creating a vacuum within said vacuum chamber, wherein said vacuum within said vacuum chamber biases said plunger and said plunger head in a retraction direction that is opposite of said discharge direction, and wherein said creating a vacuum step results from said first moving step;

exerting a separate biasing force on said plunger that also biases said plunger and said plunger head in said retraction direction;

executing second moving step after said first moving step, said second moving step comprising moving said plunger and said plunger head relative to said syringe body in said retraction direction using each of said vacuum within said vacuum chamber and said separate biasing force, wherein said vacuum within said vacuum chamber and said separate biasing force exert separate forces on said plunger that each tend to move said plunger and said plunger head in said retraction direction;

drawing fluid into said discharge chamber from said fluid source and through said fill port using said second moving step;

fluidly connecting said discharge port with said patient; and executing a third moving step after said drawing step, said third moving step comprising moving said plunger and said plunger head relative to said syringe body said discharge direction and with said plunger head interfacing with said fluid within said discharge chamber, all to discharge said fluid from said discharge chamber through said discharge port and to then inject said fluid into said patient.

2. The method of claim 1, wherein said creating a vacuum step occurs during said first moving step.

3. The method of claim 1, wherein said separate biasing force is selected from the group consisting of a pressure head in said fluid source, a spring force, a pressurization of said fluid source by a separate pressurizing source, or a combination thereof.

4. The method of claim 1, wherein said drawing step comprises directing said fluid through a check valve.

5. The method of claim 1, wherein said first moving step comprises simultaneously increasing a size of said vacuum chamber and decreasing a size of said discharge chamber.

6. The method of claim 5, wherein said second moving step comprises simultaneously decreasing said size of said vacuum chamber and increasing said size of said discharge chamber.

7. The method of claim 1, wherein said syringe body comprises a first end and said plunger comprises a plunger push rod that extends from said plunger head and beyond said first end, wherein said syringe further comprises a seal between said syringe body and said plunger push rod at said first end, and wherein said vacuum chamber is located between said plunger head and said first end.

8. The method of claim 7, wherein said first moving step comprises moving said plunger head away from said first end and toward said discharge port.

9. The method of claim 8, wherein said second moving step comprises moving said plunger head away from said fill port and toward said first end.

10. The method of claim 9, wherein said third moving step comprises moving said plunger head away from said first end and toward said discharge port.

11. A method for operating a fluid delivery system that is separate from but connectable to a patient, said fluid delivery system comprising a syringe and a separate fluid source, said syringe comprising a syringe body, a plunger comprising a plunger head disposed within said syringe body, a vacuum chamber within said syringe body, a discharge chamber within said syringe body, a fill port to said discharge chamber, and a discharge port from said discharge chamber, wherein said plunger head is disposed between and separates said discharge chamber from said vacuum chamber such that said discharge chamber and said vacuum chamber are disposed on opposite sides of said plunger head within said syringe body, and wherein said plunger head fluidly isolates said vacuum chamber from said discharge chamber, said method comprising:

executing a first moving step comprising moving said plunger and said plunger head in a first direction relative to said syringe body to create a vacuum within said vacuum chamber;

executing a second moving step after said first moving step, said second moving step comprising moving said plunger and said plunger head in a second direction relative to said syringe body, wherein a suction force from said vacuum within said vacuum chamber and a separate force each bias said plunger and said plunger head in said second direction;

drawing fluid from said fluid source, through said fill port, and into said discharge chamber using said second moving step;

fluidly connecting said discharge port with said patient; and executing a third moving step after said drawing step, wherein said third moving step comprises moving said plunger and said plunger head in said first direction and with said plunger head interfacing with said fluid within said discharge chamber, all to discharge said fluid from said discharge chamber through said discharge port and to then inject said fluid into said patient.

12. The method of claim 11, further comprising:

releasing said plunger prior to said second moving step.

13. The method of claim 11, wherein said first moving step comprises: creating said separate biasing force during said first moving step.

14. The method of claim 13, wherein said creating step comprises:
using a biasing member that comprises a first end fixed relative to said plunger and a second end fixed relative to said syringe body.

15. The method of claim 14, wherein said step of using a biasing member comprises: increasing a magnitude of a biasing force of said biasing member during said first moving step, wherein said biasing force is said separate biasing force.

16. The method of claim 15, wherein said second moving step comprises using said biasing force of said biasing member.

17. The method of claim 11, wherein said separate biasing force is a pressurizing source that is fluidly interconnected with said fluid source, and wherein said second moving step comprises: pressurizing said fluid source with said pressurizing source.

18. The method of claim 11, wherein said first moving step comprises simultaneously increasing a size of said vacuum chamber and decreasing a size of said discharge chamber.

19. The method of claim 18, wherein said second moving step comprises simultaneously decreasing said size of said vacuum chamber and increasing said size of said discharge chamber.

20. The method of claim 11, wherein said syringe body comprises a first end and said plunger comprises a plunger push rod that extends from said plunger head and beyond said first end, wherein said syringe further comprises a seal between said syringe body and said plunger push rod at said first end, and wherein said vacuum chamber is located between said plunger head and said first end.

21. The method of claim 20, wherein said first moving step comprises moving said plunger head away from said first end and toward said discharge port.

22. The method of claim 21, wherein said second moving step comprises moving said plunger head away from said fill port and toward said first end.

23. The method of claim 22, wherein said third moving step comprises moving said plunger head away from said first end and toward said discharge port.

* * * * *